(12) United States Patent
Pillai et al.

(10) Patent No.: US 8,583,249 B2
(45) Date of Patent: Nov. 12, 2013

(54) IMPLANTABLE PULSE GENERATOR FOR NEUROSTIMULATION THAT COMPRISES THIN-OXIDE TRANSISTORS AND METHOD OF OPERATING A NEUROSTIMULATION SYSTEM

(75) Inventors: N. Sateesh Pillai, Plano, TX (US); Daniel J. Black, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 330 days.

(21) Appl. No.: 12/953,986

(22) Filed: Nov. 24, 2010

(65) Prior Publication Data

US 2011/0125219 A1    May 26, 2011

Related U.S. Application Data

(60) Provisional application No. 61/264,363, filed on Nov. 25, 2009.

(51) Int. Cl.
  *A61N 1/00*    (2006.01)
(52) U.S. Cl.
  USPC .......................................................... 607/59
(58) Field of Classification Search
  USPC .......................................................... 607/59
  See application file for complete search history.

(56) References Cited

U.S. PATENT DOCUMENTS

| | | | |
|---|---|---|---|
| 5,773,968 A | 6/1998 | Kondo et al. | |
| 6,040,729 A * | 3/2000 | Sanchez et al. | ............... 327/309 |
| 6,097,237 A | 8/2000 | Singh | |
| 6,366,482 B1 | 4/2002 | Jeong | |
| 6,455,895 B1 | 9/2002 | Morishita | |
| 6,670,845 B1 | 12/2003 | Fong | |
| 6,864,718 B2 | 3/2005 | Yu | |
| 7,227,400 B1 | 6/2007 | Gillespie et al. | |
| 7,751,879 B2 | 7/2010 | Varrichio et al. | |
| 7,805,189 B2 | 9/2010 | Stein et al. | |
| 2005/0113895 A1 | 5/2005 | Danzl et al. | |
| 2006/0170486 A1 | 8/2006 | Tranchina et al. | |
| 2008/0252376 A1 | 10/2008 | Miao et al. | |
| 2009/0048643 A1 * | 2/2009 | Erickson et al. | ................ 607/59 |
| 2009/0096288 A1 * | 4/2009 | Nguyen et al. | .................. 307/31 |
| 2010/0211132 A1 | 8/2010 | Nimmagadda et al. | |

OTHER PUBLICATIONS

European Patent Office, International Search Report for PCT/US2010/058053 dated May 6, 2011.
Dhanoop Varghese, et al., "OFF-State Degradation in Drain-Extended NMOS Transistors: Interface Damage and Correlation to Dielectric Breakdown," IEEE Transactions on Electron Devices, vol. 54, No. 10, Oct. 2007, pp. 2669-2678.

* cited by examiner

*Primary Examiner* — Niketa Patel
*Assistant Examiner* — Minh Duc Pham

(57) ABSTRACT

In one embodiment, a method, of operating an IPG, comprises: generating a variable anode voltage by first circuitry to drive current during pulse generation, the first circuitry being programmable to generate the anode voltage from a plurality of voltages in response to a control signal; providing the anode voltage to a first circuit node; operating a transistor to control current flow between the first circuit node and an output of the IPG, wherein the transistor possesses a gate-to-source breakdown voltage; generating a first supply signal that is maintained at a voltage level equal to the anode voltage plus or minus a predetermined amount; and selectively applying the first supply signal and a second supply signal to a gate of the transistor to connect or disconnect the first circuit node in a circuit path with the output of the IPG.

9 Claims, 6 Drawing Sheets

IMPLANTABLE PULSE GENERATOR FOR NEUROSTIMULATION THAT COMPRISES THIN-OXIDE TRANSISTORS AND METHOD OF OPERATING A NEUROSTIMULATION SYSTEM

CROSS-REFERENCE TO RELATED APPLICATIONS

This application claims the benefit of U.S. Provisional Application No. 61/264,363, filed Nov. 25, 2009, which is incorporated herein by reference.

TECHNICAL FIELD

This application is generally related to an implantable pulse generator that employs thin oxide transistors in pulse generating circuitry.

BACKGROUND

Implantable medical devices are devices adapted for implantation within the body for treatment of one or more disorders of a patient. Common implantable medical devices include pacemakers, implantable cardioverter defibrillators (ICDs), spinal cord stimulation (SCS) systems, deep brain stimulation (DBS) systems, and peripheral nerve stimulation systems.

These types of implantable systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted adjacent or within tissue to be stimulated to deliver the electrical pulses to the appropriate tissue associated with the patient's disorder(s). The stimulation leads are then tunneled to another location within the patient's body to be electrically connected with a pulse generator or, alternatively, to an "extension."

The pulse generator is typically implanted within a subcutaneous pocket created during the implantation procedure. In many implant systems, the subcutaneous pocket is disposed in a lower back region, although subclavicular implantations and lower abdominal implantations are commonly employed for various types of therapies.

The pulse generator is typically implemented using a metallic housing that encloses circuitry for generating the electrical pulses, control circuitry, communication circuitry, a battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

SUMMARY

In one embodiment, a method, of operating an IPG, comprises: generating a variable anode voltage by first circuitry to drive current during pulse generation, the first circuitry being programmable to generate the anode voltage from a plurality of voltages in response to a control signal; providing the anode voltage to a first circuit node; operating a transistor to control current flow between the first circuit node and an output of the IPG, wherein the transistor possesses a gate-to-source breakdown voltage; generating a first supply signal that is maintained at a voltage level equal to the anode voltage plus or minus a predetermined amount; and selectively applying the first supply signal and a second supply signal to a gate of the transistor to connect or disconnect the first circuit node in a circuit path with the output of the IPG.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
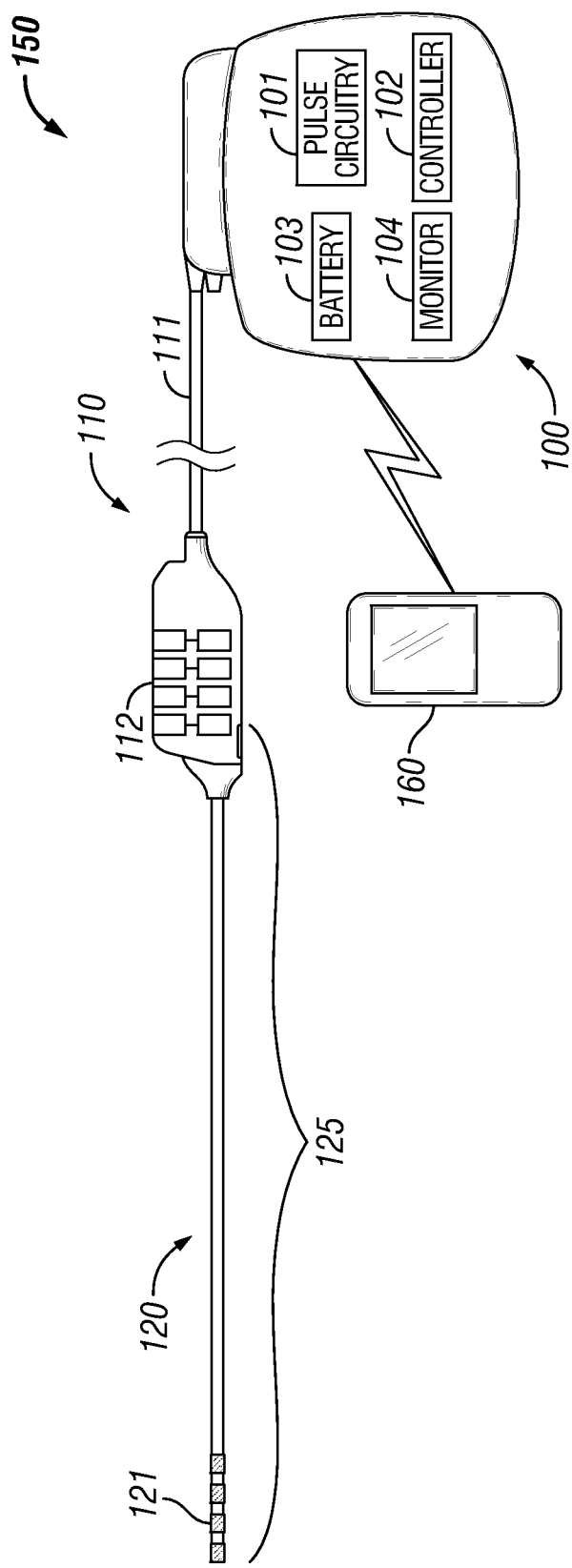
FIG. 1 depicts a stimulation system according to one representative embodiment.

FIG. 1 depicts stimulation system 150 that generates electrical pulses for application to tissue of a patient according to one embodiment. In one embodiment, system 150 is adapted to generate electrical pulses and deliver the pulses to tissue of the patient. System 150 may be adapted to stimulate any suitable tissue in a patient such as cardiac tissue, spinal cord tissue, peripheral nerve tissue, brain tissue, etc.

System 150 includes implantable pulse generator 100 that is adapted to generate electrical pulses for application to tissue of a patient. Implantable pulse generator 100 typically comprises a metallic housing that encloses pulse generating circuitry 101, controller 102, battery 103, communication circuitry (not shown), charging circuitry (not shown), etc. of the device. The controller 102 typically includes a microcontroller or other suitable processor for controlling the various other components of the device. Software code is typically stored in memory of the pulse generator 100 for execution by the microcontroller or processor to control the various components of the device.

A processor and associated charge control circuitry for an implantable pulse generator is described in U.S. patent publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference.

Stimulation system 150 further comprises one or more stimulation leads 120. Stimulation lead 120 comprises a lead body of insulative material about a plurality of conductors that extend from a proximal end of lead 120 to its distal end. The conductors electrically couple a plurality of electrodes 121 to a plurality of terminals (not shown) of lead 120. The terminals are adapted to receive electrical pulses and the electrodes 121 are adapted to apply stimulation pulses to tissue of the patient. Also, sensing of physiological signals may occur through electrodes 121, the conductors, and the terminals. Additionally or alternatively, various sensors (not shown) may be located near the distal end of stimulation lead 120 and electrically coupled to terminals through conductors within the lead body 111.

Stimulation system 150 optionally comprises extension lead 110. Extension lead 110 is adapted to connect between pulse generator 100 and stimulation lead 120. That is, electrical pulses are generated by pulse generator 100 and provided to extension lead 110 via a plurality of terminals (not shown) on the proximal end of extension lead 110. The electrical pulses are conducted through conductors within lead body 111 to housing 112. Housing 112 includes a plurality of electrical connectors (e.g., "Bal-Seal" connectors) that are adapted to connect to the terminals of lead 120. Thereby, the pulses originating from pulse generator 100 and conducted through the conductors of lead body 111 are provided to stimulation lead 120. The pulses are then conducted through the conductors of lead 120 and applied to tissue of a patient via electrodes 121.

In practice, stimulation lead 120 is implanted within a suitable location within a patient adjacent to tissue of a patient to treat the patient's particular disorder(s). The lead body extends away from the implant site and is, eventually, tunneled underneath the skin to a secondary location. Housing 112 of extension lead 110 is coupled to the terminals of lead 120 at the secondary location and is implanted at that secondary location. Lead body 111 of extension lead 110 is tunneled to a third location for connection with pulse generator 100 (which is implanted at the third location).

External controller device 160 is a device that permits the operations of pulse generator 100 to be controlled by a clinician or a patient after pulse generator 100 is implanted within a patient. Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the clinician and using the wireless communication capabilities to conduct communications with IPG 100.

Controller device 160 provides one or more user interfaces that are adapted to allow a clinician to efficiently define one or more stimulation programs to treat the patient's disorder(s). Each stimulation program may include one or more sets of stimulation parameters including pulse amplitude, pulse width, pulse frequency, etc. IPG 100 modifies its internal parameters in response to the control signals from controller device 160 to vary the stimulation characteristics of stimulation pulses transmitted through stimulation lead 120 to the tissue of the patient.

Figure 2:
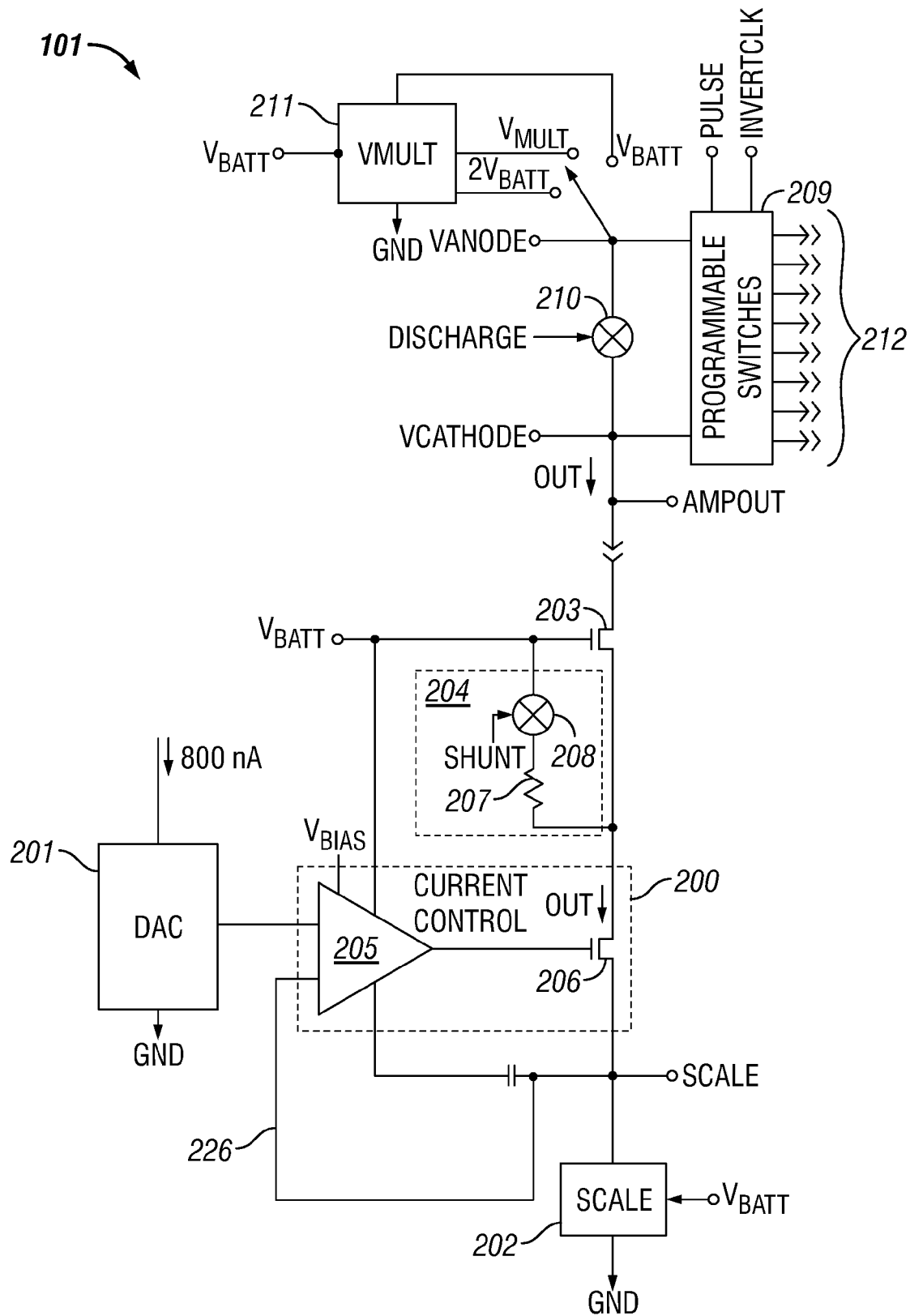
FIG. 2 depicts pulse generating circuitry that may be employed according to some representative embodiments.

Referring to FIG. 2, pulse generating circuitry 101 is shown in greater detail according to one representative embodiment. FIG. 2 depicts pulse generating circuitry 101 in the form of a simplified equivalent circuit diagram for portions of the respective circuitry. Although pulse generating circuitry 101 is a "single channel" designed for providing constant current pulses, any suitable type of pulse generating circuitry may be employed including constant current, constant voltage, multiple-independent current or voltage sources, etc.

As shown in FIG. 2, the current control circuit 200 within driver 226 includes an operational amplifier (op-amp) 205. The output of the operational amplifier 205 is connected to the gate of a field effect transistor (FET) 206. One terminal of transistor 206 is connected to a terminal of a high voltage protection source-follower configured transistor 203 and, through a shunt resistor 207 and a shunt switch 208 forming the shunt circuit 204, to the battery voltage $V_{BATT}$.

The other terminal of transistor 203 is connected to the AMPOUT signal, which in turn is coupled to the VCATHODE signal. The VCATHODE signal is connected by one of switches 209 to an electrode or optionally by switch 210 to a VANODE signal, corresponding to the voltage driven on the selected anode electrode. The VANODE signal is connected by one of programmable switches 209 to an electrode, and selectively to one of (a) the $V_{BATT}$ voltage, available on an output of the voltage multiplier 211, (b) the $V_{MULT}$ voltage generated by voltage multiplier 211 or (c) the $2V_{BATT}$ voltage generated by voltage multiplier 211.

The other terminal of transistor 206 (the one not connected to transistor 203) is connected to the SCALE input signal, to one input of operational amplifier 205, and to one terminal of scale circuit 202. Scale circuit 202 may be implemented, for example, by a digitally-controlled resistance that may be selectively varied. The variable output of scale circuit 202 is also connected to the same input of operational amplifier 205 as the terminal of transistor 206 and the SCALE input signal. The other terminal of scale circuit 202 is coupled to ground.

The variable output terminal of digital-to-analog converter 201 is connected to the other input of operational amplifier 205. The other terminal of digital-to-analog converter 201 is connected to a current mirror (not shown) transmitting a bias current of approximately 800 nA through the digital-to-analog converter 201 to ground. The implementation of digital-to-analog converter 201 is selected for monotonicity of the output function (e.g., a ladder resistor).

Current control 200 sets the amplitude of output current $I_{OUT}$ driven for the electrical stimulation pulse. Each of the outputs 212 for programmable switches 209 is connected through a capacitor (not shown) to one of the electrodes. Switches 209 programmably connect, with timing controlled by input signals PULSE and INVERTCLK, one or more of the electrodes to the anode voltage VANODE and one or more of the electrodes to the cathode voltage VCATHODE to deliver the electrical stimulation pulse to the desired location(s). In addition, each of outputs 212 may be selectively tri-stated (set to a high-impedance state), so that each electrode may be connected as an anode, connected as a cathode, or tri-stated (off).

During operation, driver 226 stores switching patterns for controlling connection of switch outputs 212 within a memory (not shown). The switching patterns define parameters for electrical stimulation pulses, including the lead electrode to be employed as anode and as cathode. For delivery of an electrical stimulation pulse according to embodiments of the invention, switches 209 connect at least one of the outputs 212 to the selected anode voltage VANODE, and at least one other of the outputs 212 to a cathode voltage VCATHODE (which is also the output voltage AMPOUT that may be employed for selective monitoring of any output pulse delivered). In this manner, an electrical pulse is selectively transmitted through selected one(s) of the electrodes and returned through other selected one(s) of the electrodes for delivery of that electrical pulse to the desired stimulation site(s) according to an embodiment.

The functionality of driver 226 also includes inversion of the switching pattern(s) retrieved from the memory so that the previously selected anode electrode(s) becomes the cathode electrode(s) and the previously selected cathode electrode(s) becomes the anode electrode(s) (and all other electrodes remain unused). This functionality is employed for active discharge, where pulses of opposite polarity are provided to discharge capacitors coupled to the outputs of the IPG.

Driver 226 also controls anode source voltage selection, selecting the anode voltage VANODE from one of twice a battery voltage $2V_{BATT}$, a voltage multiplier output voltage $V_{MULT}$, and the battery voltage $V_{BATT}$, all generated by capacitive voltage multiplier ($V_{Mult}$) 211.

Switches 209 are also employed to provide transition blanking, controlled one clock cycle blanking of the anode electrodes within the lead 120 upon a signal change for patient safety. Such blanking may be accomplished by selectively tri-stating the outputs 212 to provide blanking without altering the stored memory or register switching patterns. During delivery of an electrical stimulation pulse, switch 210, controlled by an input signal DISCHARGE, is normally open, between pulses, switch 210 is closed to allow passive discharge of the capacitive connections between outputs 212 and corresponding electrodes.

Additional discussion of pulse generation is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference, although any suitable type of pulse generating circuitry may be employed including constant current, constant voltage, multiple-independent current or voltage sources, etc.

In conventional circuit designs for neurostimulation systems, pulse generating circuitry is implemented, in part, using an integrated circuit. The conventional integrated circuit employs relatively thick-oxide gates for transistors to perform switching of high voltage signals. Specifically, signals up to 20V may be necessary to achieve a suitable amount of current for some stimulation therapies. The thick oxide is employed largely to protect against physically damaging the oxide by excessive voltages in the circuitry.

Figure 3:
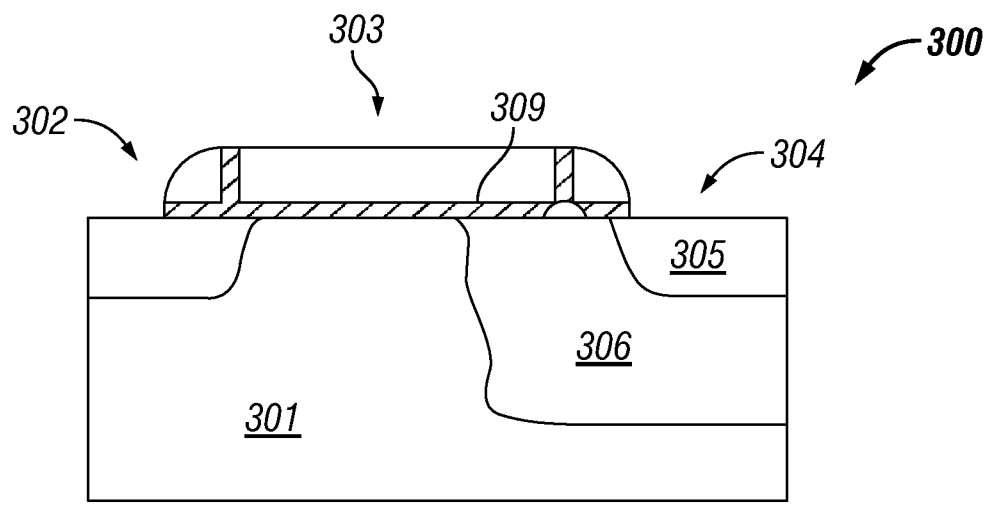
FIG. 3 depicts a drain extended transistor that may be employed according to some representative embodiments.

Some representative embodiments employ thin-oxide transistors to perform switching of high voltage signals for generation of stimulation pulses. Although some embodiments are adapted to pass 20V signals, alternative embodiments may be adapted to pass any suitable voltage level including 10V, 12V, 15V, and 25V as examples. FIG. 3 depicts thin oxide, drain extended transistor 300 for use in pulse generating circuitry according to one representative embodiment.

In the example of FIG. 3, transistor 300 is an N-channel drain-extended transistor (DENMOS). An n-type source 302 is formed within the p-well 301, where the p-well 301 provides a p-type channel region between the source and an extended n-type drain 304. The extended drain includes an n-type drain 305 implanted within the n-well 306, and a drift region in the n-well 306 extending between the channel region and the drain 304. The device drain region is spaced from the channel (e.g., extended) to provide a drift region or drain extension in the n-type semiconductor material therebetween. In operation, the spacing of the drain and the channel spreads out the electric fields, thereby increasing the breakdown voltage rating of the device (higher $B_{Vdas}$). In some embodiments, the channel is isolated from the substrate, e.g., by means of an n-type isolation ring (not shown) which is electrically isolated from the drain.

A gate dielectric or oxide layer 309 is formed over the channel of transistor 300, and it may be an oxide, a thermally grown silicon dioxide, a nitride, an oxynitride, or a combination of these or other insulators. A gate conductor is formed over gate dielectric 309. The gate signal is applied to gate 303 to control transistor 300. Specifically, the gate-to-source potential ($V_{gs}$) controls the free carriers and, hence, resistance in the channel of transistor 300. Although one typical drain extended structure is shown in FIG. 3, any suitable known or later-developed adaption of transistors to include drain extensions may be employed according to alternative embodiments.

As previously mentioned, conventional neurostimulation systems employ FETs with thick oxides to prevent a high voltage difference between the gate and the source from physically damaging the oxide layer. In contrast, some representative embodiments employ gating signals that ensure that the voltage difference between the gate and the source is maintained within a range to prevent damage of oxide layer 309. Some embodiments adapt the various circuitry to prevent gate signals from causing irreversible damage to the circuitry as discussed below.

Figure 4:
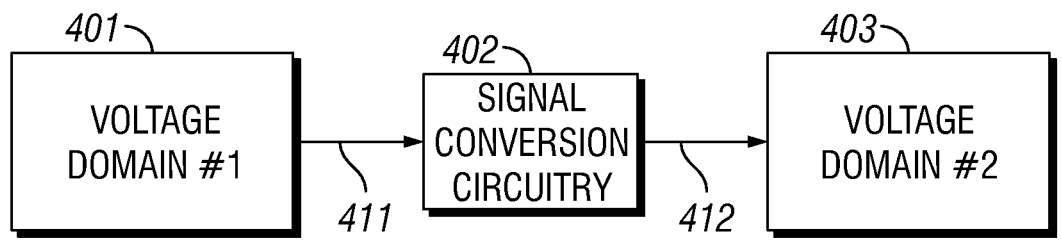
FIG. 4 depicts respective voltage domains and conversion circuitry for converting logic signals between the respective voltage domains according to one representative embodiment.

Additionally, certain embodiments divide portions of the pulse generating circuitry 101 into different "voltage domains" 401 and 403 as shown in FIG. 4. For the purposes of this application, a "voltage domain" refers to a set of circuits that operates according to a given pair of logic signals where a voltage value is defined for a "plus" logic state and another voltage value is defined for a "minus" logic state. The voltage conversion may occur between any suitable sets of voltages. Also, in some embodiments, the voltage conversion may involve communication of logic states between respective domains with one or more voltage domains including logic levels below ground.

Voltage domain 401 comprises one or more circuits including one or more transistors with gates that are controlled by respective logic signals. In one embodiment, one or more transistors in voltage domain 401 are gated by a 0V signal for a logic minus signal and by a 4V signal from a logic plus signal. Voltage domain 401 may also output signal a logic signal according to the voltages of domain 401 (e.g., 0V and 4V).

Figure 5:
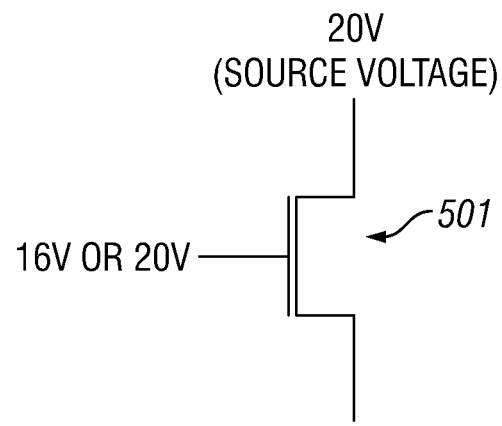
FIG. 5 depicts a transistor within the high voltage domain of FIG. 4 according to one representative embodiment.

Likewise, voltage domain 403 comprises one or more circuits including one or more transistors with gates that are controlled by respective logic signals. In one embodiment, one or more transistors in voltage domain 403 are gated by a 16V signal for a logic minus signal and by a 20V signal for a logic plus signal. The higher voltage signals used for gating in voltage domain 403 permit higher voltage signals to be provided to the transistors of domain 403 (e.g., without causing irreversible damage of the transistors). The voltage difference between the sources and the gates of transistors in domain 403 is kept within a range that prevents damage to the oxide layers of the transistors. FIG. 5 depicts transistor 501 for operation in voltage domain 403. Transistor 501 is employed to gate a high voltage signal (e.g., a voltage signal, from the voltage multiplier, being used to drive current through tissue of the patient via electrodes of system 150). The source voltage may be 20V as shown in FIG. 5, although any other suitable source voltage may be employed for other embodiments. The logic signals applied to the gate of transistor 501 are 16V for a logic minus signal and 20V for a logic plus signal.

The values of these signals may vary depending upon the transistor type. For example, a gating supply signal may be generated to vary from the source voltage being passed by plus or minus a predetermined amount. Since the source signal is 20V, the selection of the 16V and 20V gating signals in this case keeps the voltage between the gate and source within a range that prevents damage to the oxide layer of gate 501 (e.g., less than the 5V rating of typical thin oxide layers). Although 5V-oxide transistors are contemplated for some embodiments, any suitable transistors with other gate voltage gate characteristics may be alternatively employed, such as 1.8V-oxide transistors. The selection of the levels for the logic signals will depend upon the gate voltage characteristics of the transistors of the domains and the voltage to be passed by the transistors. In some alternative embodiments, transistors with different characteristics may be selected for the different domains.

Signal 411 is provided from domain 401 to signal conversion circuitry 402. Signal conversion circuitry 402 converts signal 411 into a signal suitable for voltage domain 403. That is, when signal 411 is a logic minus signal according voltage domain 401, conversion circuitry 402 outputs a logic minus signal according to the logic voltages of logic domain 403. Similarly, when signal 411 is a logic plus signal according to voltage domain 401, conversion circuitry 402 outputs a logic plus signal according to voltage domain 403.

Figure 6:
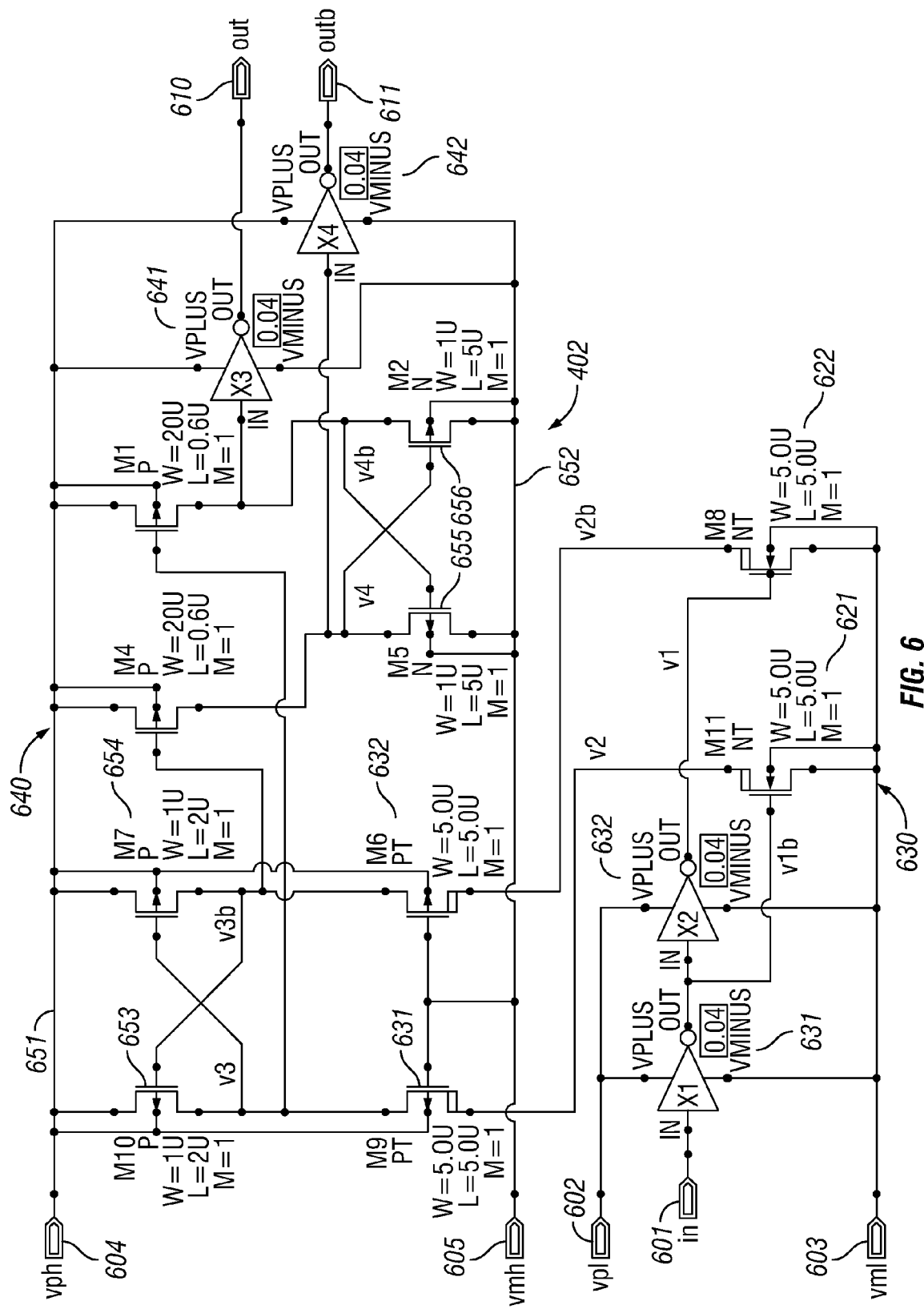
FIG. 6 depicts logic signal conversion circuitry according to one representative embodiment.

FIG. 6 depicts conversion circuitry 402 according to one representative embodiment. In FIG. 6 (and FIG. 7), n-type transistors are denoted by the "N" symbol and p-type transistors are denoted by the "P" symbol. Conversion circuitry 402 comprises input 601 for receiving logic signal from a low voltage logic domain (e.g., with respective logic signals at 0V and 4V). The received input signal is a control signal generated by the low voltage logic domain for provision to circuitry in the high voltage logic domain. Conversion circuitry 402 further comprises inputs 602 and 603 for receiving logic signals used within the low voltage domain such as domain 401. The logic plus signal is provided to input 602 and the logic minus signal is provided to input 603. Similarly, conversion circuitry 402 further comprises inputs 604 and 605 for receiving logic signals used within a high voltage domain such as domain 403. The logic plus signal is provided to input 604 and the logic minus signal is provided to input 605.

In operation, conversion circuitry 402 comprises first stage 630 and second stage 640. In first stage, the input logic signal received from the low voltage domain is provided to inverter 631 which is also connected to a second inverter 632. The outputs of inverters 631 and 632 are provided to the gates of drain extended transistors 621 and 622, respectively. Drain extended transistors 621 and 622 are connected to drain extended transistors 631 and 632 of second stage 640. The drain extensions of transistors 621, 622, 631, and 632 are employed to transition between the low voltage signals in stage 630 to the high voltage signals in stage 640. The drain extensions of transistors 621, 622, 631, and 632 protect the respective gates from damage due to high voltage differences between signals in the respective stages. Accordingly, the thin oxide gates of the transistors in stages 630 and 640 are not subjected to possible damage due to high voltage differences.

The various transistors of conversion circuitry 402 are arranged such that when the signal provided to input 601 is a logic plus signal according to domain 401, the signal provided to inverter 641 is low and inverter 641 outputs the signal received via input 604 (e.g., a logic plus signal according to domain 403). Inverter 642 outputs the complement of the output of inverter 641. Likewise, the various transistors of conversion circuitry 402 are arranged such that when the signal provided to input 601 is a logic minus signal according to domain 401, the signal provided to inverter 641 is high and inverter 641 outputs signal received via input 605 (i.e., a logic minus signal according to domain 403). Accordingly, in the embodiment shown in FIG. 6, conversion circuitry performs "rail to rail" logic shifting. Also, in some embodiments, the logic shifting of conversion circuitry 403 is performed without a constant current draw. The embodiment shown in FIG. 6 consumes power only when switching.

In the embodiment shown in FIG. 6, the circuitry for obtaining rail to rail logic shifts includes cross-coupled transistor sets 651 and 652. Transistor set 651 includes p-type transistors 653 and 654 which are cross coupled in that the gate of each transistor is connected to the drain of the other transistor. The arrangement ensures opposite polarity of each side of the transistor set. Transistors 653 and 654 are connected to the circuit node receiving input 604. Transistors 653 and 654 are also respectively connected to p-type transistors 631 and 632, which in turn are connected to the circuit node receiving input 605. Transistor set 652, including n-type transistors 655 and 656, is arranged in a similar manner to transistor set 651 to obtain opposite polarities. Transistors 655 and 656 are respectively connected to p-type transistors 657 and 658 and to the circuit node coupled to input 605. The additional transistor set 652 is employed to get to the bottom logic rail for the logic level conversion.

Figure 7:
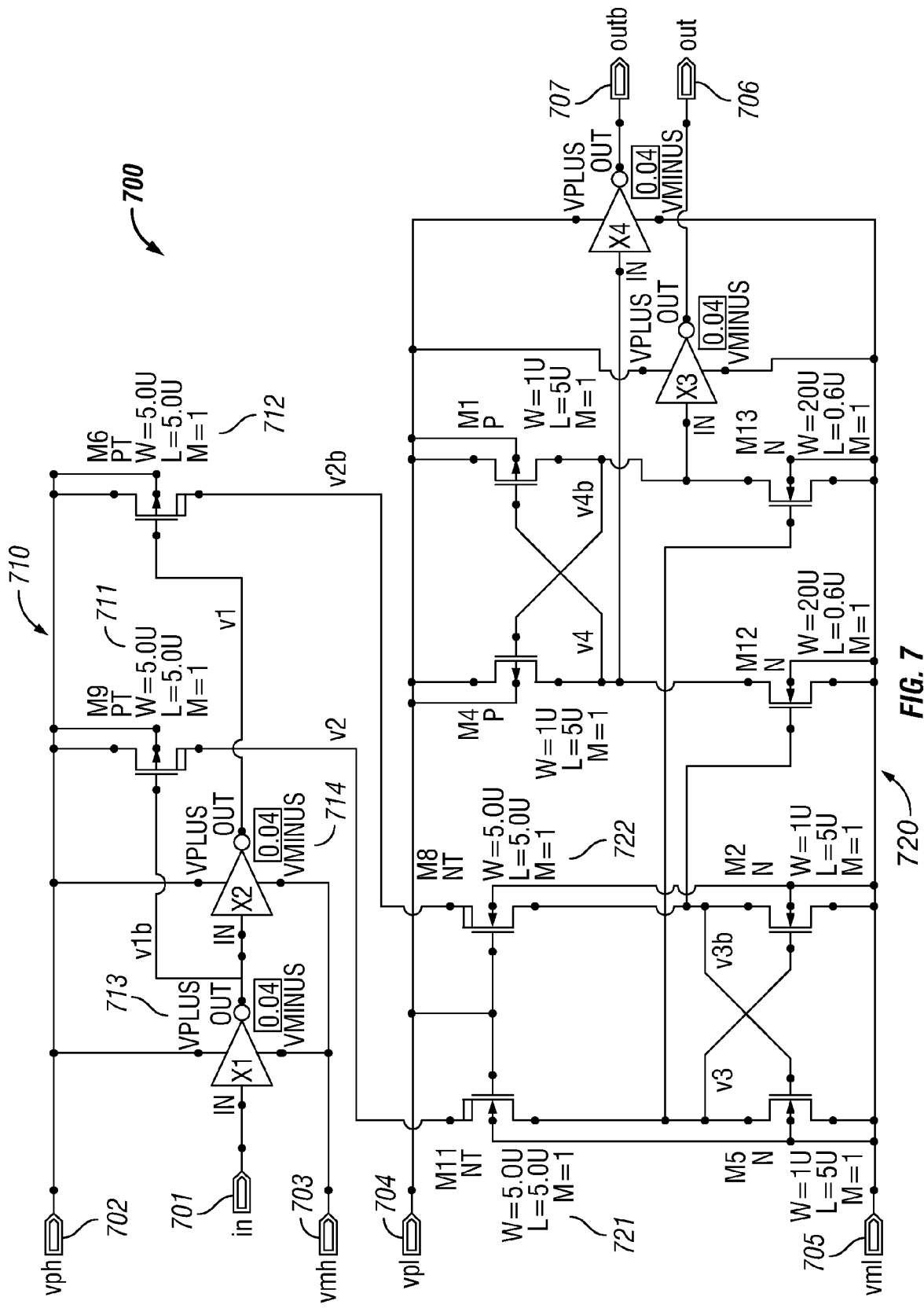
FIG. 7 depicts logic signal conversion circuitry according to one representative embodiment.

FIG. 7 depicts voltage conversion circuitry 700 for converting a logic signal from high voltage domain 403 to a logic signal appropriate for low voltage domain 401. Conversion circuitry 700 operates in a similar, but complementary manner, to circuitry 402. Conversion circuitry 700 receives input signal 701 and compares input signal 701 to the signals from inputs 702 and 703 using inverters 713 and 714, respectively. Inputs 702 and 703 are used to receive the logic minus and plus signals from the high voltage domain.

Conversion circuitry 700 comprises two stages 710 and 720. High voltage signals are present in stage 710 and low voltage signals are present in stage 720. Drain extended transistors 711 and 712 in stage 710 are connected to drain extended transistors 721 and 722 in stage 720. Drain extended transistors 711, 712, 721, and 722 are employed to transition between the high voltage signals in stage 710 to the low voltage signals in stage 720. Accordingly, the thin oxide gates of the transistors in stages 710 and 720 are not subjected to possible damage due to high voltage differences.

When the signal from input 701 is a logic plus signal according to the high voltage domain, conversion circuitry 700 outputs on output 706 a signal that is a logic plus signal according to the low voltage domain. When the signal from input 701 is a logic minus signal according to the high voltage domain, conversion circuitry 700 outputs on output 706 a signal that is a logic minus signal according to the low voltage domain. The logic complement of output 706 is output by conversion circuitry 700 on output 707.

In some embodiments, thin oxide transistors are employed to selectively couple anode and cathode voltages to respective circuit nodes in the pulse generator. For example, in FIG. 2, transistors within programmable switches 209 may be fabricated using thin-oxide gates. As previously discussed, suitable voltage signals for controlling the gates of such transistors are generated and applied to avoid overstress of the oxide of the transistors.

Figure 8:
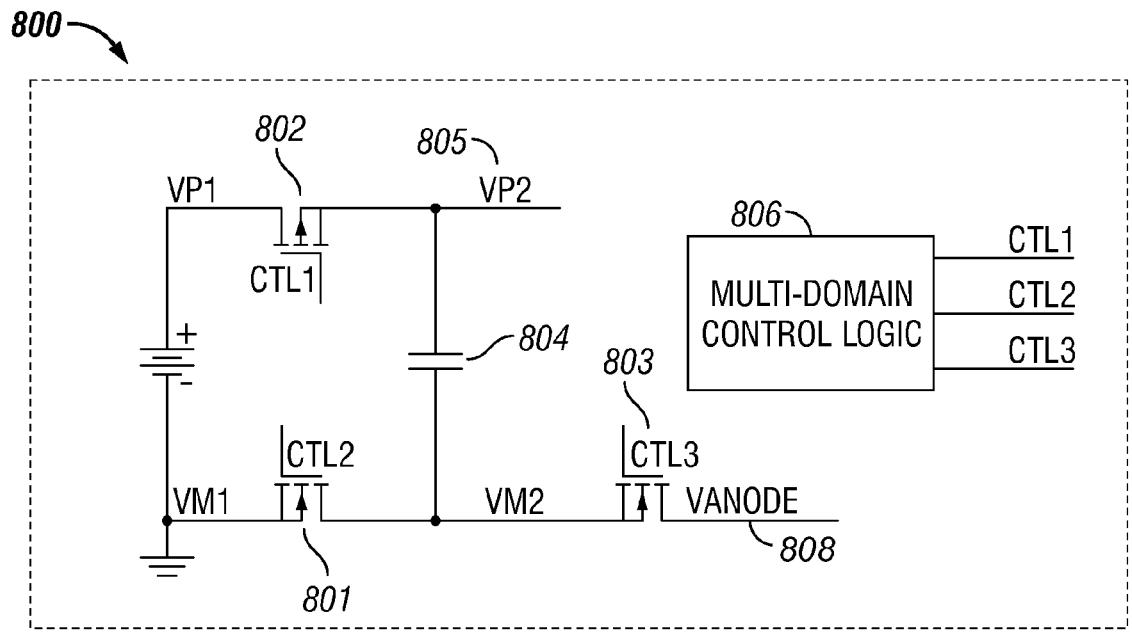
FIG. 8 depicts circuitry for generating a supply signal for gating operations based upon a reference signal according to one representative embodiment.

FIG. 8 depicts circuitry 800 for creating a supply signal relative to a particular reference voltage (VANODE, for example, as shown in FIG. 8) for use, in an example, as a gate signal according to some embodiments. Circuitry 800 is operated in successive cycles to generate the appropriate reference voltage. In the first cycle, switches 801 and 802 are closed. This copies an existing voltage difference onto capacitor 804. The existing voltage difference may be the difference between plus and minus logic levels (VP1-VM1) suitable for controlling the respective transistors. In some embodiments, the voltage difference is provided by the system battery.

In the next cycle of operation, switches 801 and 802 are opened and switch 803 is closed. This refers the copied voltage difference to a reference voltage 808 (VANODE, in this example, see FIG. 2). The new supply voltage 805 (VP2) for gating operations is now in the proper range to control switches that can suitably pass the reference voltage 808.

The control signals for the different switches 801, 802, and 803 of circuitry 800 are generated by multi-domain control logic 806. When using thin-oxide transistors in circuitry 800, the control signals, in turn, are referenced to the appropriate signal(s) being controlled by switches 801, 802, and 803 by control logic 806. Also, the control signals are asserted in the correct order by control logic 806 (e.g., using a suitable state-machine implementation).

In some embodiments, two sets of circuitry 800 are employed within pulse generator 100. One set of circuitry 800 is employed to generate a gating signal reference to VANODE. The second set of corresponding circuitry 800 is employed to generate a gating signal reference to VCATHODE (see FIG. 2). One or both of the gating signals may be offset (plus or minus depending upon the transistor type) from the voltage to be passed by a predetermined amount.

Figure 9:
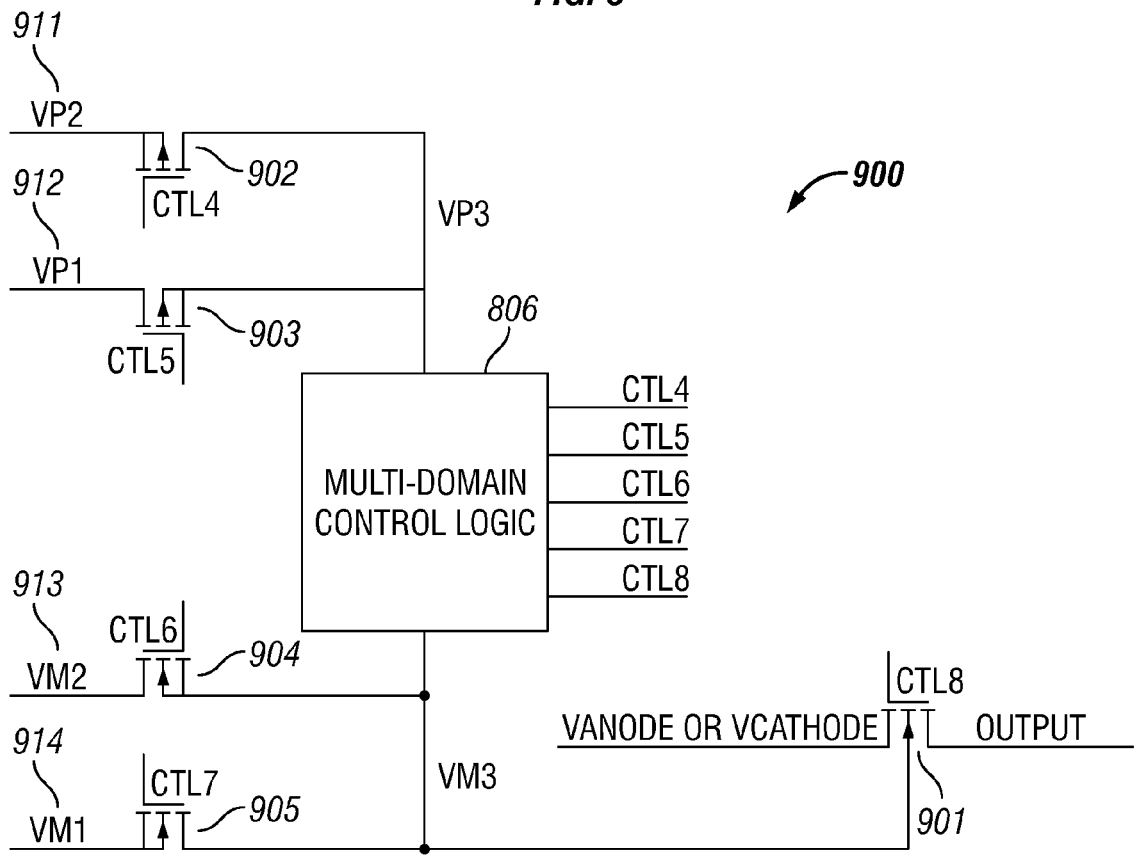
FIG. 9 depicts circuitry for controlling the coupling of a node in pulse generating circuitry with an output of a pulse generator according to one representative embodiment.

In some embodiments as shown in FIG. 9, multi-domain control logic 806 further controls application of a respective supply signal to control an individual switch 901 in programmable switches 209 of pulse generator 100. Switch 901 is disposed between a respective node in the pulse generation circuitry (VANODE or VCATHODE) and an output 212 of the pulse generator. Each switch 901 of the set of switches 209 can be controlled in a similar manner.

In the one embodiment shown in FIG. 9, it is noted that in order to turn on output switch 901 without overstressing the oxide, the gate and body (or back-gate) are referenced to the voltage being passed (e.g. VANODE or VCATHODE). However, in order to fully turn off the switch 901, both the gate and body are referenced to the lowest possible voltage (e.g., ground). Otherwise, a voltage on VANODE or OUTPUT that is lower than the device body could activate a parasitic diode, effectively turning on switch 901.

Multi-domain control logic 806 provides a supply or gate signal to switch 901 that varies in relation to the state selected for switch 901 and the voltage of the signal being passed by switch 901. Multi-domain control logic 806 is connected to input line 912 for VP1 (voltage "plus" level for domain one) and to input line 911 for VP2 (voltage "plus" level for domain two). Likewise, multi-domain control logic 806 is connected to input line 914 for VM1 (voltage "minus" level for domain one) and to input line 913 for VM2 (voltage "minus" level for domain two). Multi-domain control logic 806 provides control signals to switches 911-914 to control the signal provide to the gate of switch 901 from the various input lines 911-914. That is, during time periods of pulse generation when a high voltage is provided via VANODE and switch 901, multi-domain logic 806 may select an appropriate logic signal from VP2 and VM2. Alternatively, during other time periods when a high voltage is not provided via VANODE and switch 901, multi-domain logic 806 may select an appropriate logic signal from VP1 and VM1.

The circuitry shown in FIGS. 8 and 9 are adapted for implementation using NMOS output switches. Appropriate supplies and control for PMOS switches could be provided to perform equivalent operations according to alternative embodiments. Other embodiments may include different variations on the devices and circuit configurations previously discussed. For example, depletion mode transistors with thin oxide gates may be controlled to pass high voltage signals using suitable gate signals according to alternative embodiments where the gate signals are controlled to prevent over-stressing the oxide. Also, dynamic supply generation circuitry may be implemented for voltage domains below ground for alternative embodiments.

In some embodiments, voltage multiplier 211 is adapted to provide supply signals that are offset from an output of voltage multiplier 211 by a predetermined amount. For example, voltage multiplier 211 could be adapted to provide a supply signal that equals $V_{MULT}$+5V. This supply signal may be employed to control transistors in IPG 100 that pass the VANODE signal. The voltage multiplier may create the additional supply signal by including an additional storage capacitor. During a charging phase of operation of the multiplier 211, this additional storage capacitor is charged until it reaches a voltage of 5V. During an output phase, the additional storage capacitor is placed in series with the $V_{MULT}$ output to generate the respective supply signal.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of operating an implantable pulse generator (IPG) for stimulation of tissue of a patient, the method comprising:

generating a variable anode voltage by first circuitry to drive current during generation of respective electrical pulses, the first circuitry being programmable to generate the anode voltage from a plurality of voltages in response to a control signal;

providing the anode voltage to a first circuit node during generation of the respective electrical pulses;

operating a transistor to control current flow between the first circuit node and an output of the IPG during generation of the respective electrical pulses, wherein the transistor possesses a gate-to-source breakdown voltage and a maximum voltage from the plurality of voltages employed for the anode voltage exceeds the gate-to-source breakdown voltage of the transistor;

generating a first supply signal that is maintained at a voltage level equal to the anode voltage plus or minus a predetermined amount; and selectively applying the first supply signal and a second supply signal to a gate of the transistor to connect or disconnect the first circuit node in a circuit path with the output of the IPG during generation of the respective pulses, wherein the difference between the first supply signal and the anode voltage is less than the gate-to-source breakdown voltage of the transistor.

2. The method of claim 1 wherein the anode voltage and the first supply signal are varied during generation of the respective pulses according to amplitude parameters in respective sets of parameters of a multi-stimulation set program executed by the IPG.

3. The method of claim 1 further comprising:

operating circuitry to control current through the output such that substantially constant current is provided during a respective pulse.

4. The method of claim 1 wherein the transistor has a gate-to-source breakdown voltage of approximately 5V and the anode voltage exceeds 10V.

5. The method of claim 1 wherein the anode voltage is provided by a voltage multiplier that dynamically generates the anode voltage under control of a controller of the IPG.

6. The method of claim 5 wherein the voltage multiplier outputs a maximum voltage of approximately 20V under the control of the controller.

7. The method of claim 1 wherein the first and second supply signals are provided to the transistor during first time periods and wherein the selectively providing further comprises:

providing a third supply signal to the transistor, the third supply signal adapted to prevent a parasitic diode effect from turning the transistor to an on-state during second time periods.

8. The method of claim 1 wherein the transistor is contained within a digital-to-analog converter with one or more intermediate circuit elements disposed between the transistor and the output of the IPG.

9. The method of claim 1 wherein the transistor is connected to a circuit trace, the circuit trace is connected a capacitor, the capacitor is connected to a feed-through wire, and the feed-through wire is connected to an electrical connector within the header of the IPG that is adapted for connection to a terminal contact of a stimulation lead.

* * * * *